United States Patent
Li et al.

(10) Patent No.: US 11,793,763 B2
(45) Date of Patent: Oct. 24, 2023

(54) WATER-SOLUBLE LUTEIN ESTER MICROCAPSULES AND A METHOD OF PREPARING THE SAME

(71) Applicants: Honglong Li, Luohe (CN); Ziheng Jin, Luohe (CN); Xiaosong Xu, Luohe (CN); Linzheng Li, Luohe (CN); Wenjin Zhang, Luohe (CN); Chunfeng Yu, Luohe (CN); Huiting Xia, Luohe (CN)

(72) Inventors: Honglong Li, Luohe (CN); Ziheng Jin, Luohe (CN); Xiaosong Xu, Luohe (CN); Linzheng Li, Luohe (CN); Wenjin Zhang, Luohe (CN); Chunfeng Yu, Luohe (CN); Huiting Xia, Luohe (CN)

(73) Assignee: HENAN ZHONGDA HENGYUAN BIOTECHNOLOGY STOCK CO., LTD., Henan (CN)

(*) Notice: Subject to any disclaimer, the term of this patent is extended or adjusted under 35 U.S.C. 154(b) by 54 days.

(21) Appl. No.: 17/340,292

(22) Filed: Jun. 7, 2021

(65) Prior Publication Data
US 2021/0401761 A1     Dec. 30, 2021

(30) Foreign Application Priority Data
Jun. 29, 2020  (CN) .......................... 202010603864.8

(51) Int. Cl.
*A61K 9/16* (2006.01)
*A23L 33/105* (2016.01)
*A61K 31/21* (2006.01)
*A61K 36/28* (2006.01)
*A61K 9/50* (2006.01)

(52) U.S. Cl.
CPC .......... *A61K 9/5089* (2013.01); *A61K 9/5026* (2013.01); *A61K 9/5063* (2013.01)

(58) Field of Classification Search
CPC .. A61K 9/5089; A61K 9/5026; A61K 9/5063; A61K 9/1623; A61K 9/0053; A61K 9/1617; A61K 9/1652; A61K 9/1664; A61K 31/21; A61K 36/28; A23L 33/105; A61P 1/00
See application file for complete search history.

(56) References Cited

FOREIGN PATENT DOCUMENTS

CN         109305931 A  *  2/2019
WO    WO-9106292 A1  *  5/1991

OTHER PUBLICATIONS

Varaporn et al., Effect of Process Variables on the Microencapsulation of Vitamin A Palmitate by Gelatin-Acacia Coacervation, Drug Development and Industrial Pharmacy, 27:6, 561-566. (Year: 2001).*

* cited by examiner

*Primary Examiner* — Abigail Vanhorn

(57) ABSTRACT

A method of preparing water-soluble lutein ester microcapsules includes: mixing marigold flower particles with an extracting solvent, refluxing at 65-85° C.; removing the extracting solvent to obtain a crude extract; washing the crude extract with a washing solvent; removing the washing solvent to obtain a crude lutein ester; adding an oil-phase antioxidant and a vegetable oil to the crude lutein ester, mixing and heating at 90-100° C. to obtain a lutein ester oil phase; adding a wall material, an emulsifier, a water-phase antioxidant, and a water-phase filler into water, and heating to obtain a water phase; adding the lutein ester oil phase to the water phase under a high-speed shearing, mixing evenly, and homogenizing to obtain a lutein ester emulsion; drying twice to obtain semi-finished lutein ester microcapsules; and solidifying to obtain the lutein ester microcapsules. Water-soluble lutein ester microcapsules prepared by the method are also disclosed.

1 Claim, No Drawings

WATER-SOLUBLE LUTEIN ESTER MICROCAPSULES AND A METHOD OF PREPARING THE SAME

This application claims priority to Chinese Patent Application No. 202010603864.8, filed on Jun. 29, 2020, which is incorporated by reference for all purposes as if fully set forth herein.

TECHNICAL FIELD

The present invention relates to the technical field of processing of biologically active substances, and specifically relates to a method for extracting lutein esters and a method for preparing water-soluble lutein ester microcapsules.

BACKGROUND TECHNIQUE

Marigold (Tagetes erecta L) is native to Mexico. It is distributed all over China. It can grow in areas from 1150 meters to 1480 meters above sea level. It has large flowers and long flowering period. It is also often used in flower beds. The medicinal value of its flowers includes: reducing fever and detoxification, resolving phlegm and relieving cough; using as a fragrance; previously being used as an antibacterial, sedative, and antispasmodic agent. Tagetes-minuta (T. glanduliflora) of the same genus contains volatile oil, which has sedative, antihypertensive, bronchial expansion, antispasmodic and anti-inflammatory effects.

Lutein ester is a carotenoid fatty acid ester. Its chemical name is lutein dipalmitate. It is easily soluble in organic solvents. It is widely found in corn, cabbage, marigold and other plants. Among them, it is the most abundant in marigold. Lutein ester is the main component of the retina and macular area of the human eye. It has strong antioxidant capacity, prevents free radicals from oxidative damage to the eye, improves eye microcirculation, prevents senile cataracts, protects the retina, and prevents optic nerve atrophy. Lutein ester must be taken from food.

Lutein ester is a compound formed by lutein and one or two molecules of fatty acid. Its stability is stronger than that of lutein. It will only decompose under high temperature, strong acid, and oxidation conditions. Lutein ester contains fatty acid groups and can be naturally hydrolyzed into free lutein in the human body, which is easy to absorb. Its bioavailability is much higher than that of lutein crystals. Most of the lutein health products on the market currently use lutein ester as the main functional raw material.

Microencapsulation technology is a pharmacological method that effectively improves the stability and solubility of drugs. The core material is wrapped in a capsule composed of a wall material, and the active ingredients of the core material are preserved from the influence of external adverse factors. The storage time of the core material controls the release of the core material. A twice embedding (drying twice) is to embed the core material twice during a drying process on the basis of a primary embedding (emulsification). The drying temperature is low and the core material is avoided being destroyed at high temperature. The obtained particles are more stable than traditional spray-dried particles, have a longer storage period, and are more controllable core material release.

The inventors of the present application, however, found that the above-mentioned technology has at least the following technical problems in implementing the embodiments of the present application:

(1) In the prior art, the process of using high-purity lutein ester crystals for microencapsulation requires a lot of equipment, particularly complex refining equipment, which leads to a substantial increase in production costs;

(2) In the prior art, it is necessary to use high-purity lutein ester crystals, but the higher the purity of the lutein ester crystals, the higher the requirements for transportation and storage conditions, which further increases the production cost. To reduce production costs has become an important topic for those skilled in the art.

SUMMARY OF THE INVENTION

In order to overcome the problem of high cost in the large-scale mass production of lutein ester microcapsules, the examples of this application provide a method for extracting lutein esters and preparing lutein ester microcapsules. First, lutein ester is obtained by extracting from marigold flower particles, and then a series of steps are used to prepare lutein ester microcapsules. In the present invention, lutein ester is extracted from marigold flower particles, and then concentrated, washed, and removed to obtain lutein ester. Lutein ester is prepared by a series of processes to obtain lutein ester microcapsules. Among them, lutein ester is extracted from marigold flower particles, which are economical and easy to obtain. There is no separation and purification, which retains part of the medicinal value of marigold flower, increases the health benefits of lutein ester. The use of a twice embedding (drying twice) method (drying twice) can also make the prepared capsules more stable and easier to store, and is suitable for food, medicine and other fields.

The technical solutions adopted by the embodiments of this application to solve the technical problems are:

A method of preparing water-soluble lutein ester microcapsules includes: mixing marigold flower particles with an extracting solvent, refluxing at 65-85° C.; removing the extracting solvent to obtain a crude extract; washing the crude extract with a washing solvent; removing the washing solvent to obtain a crude lutein ester; adding an oil-phase antioxidant and a vegetable oil to the crude lutein ester, mixing and heating at 90-100° C. to obtain a lutein ester oil phase; adding a wall material, an emulsifier, a water-phase antioxidant, and a water-phase filler into water, and heating to obtain a water phase; adding the lutein ester oil phase to the water phase under a high-speed shearing, mixing evenly, and homogenizing by a high-pressure homogenizer to obtain a lutein ester emulsion; drying the lutein ester emulsion twice to obtain semi-finished lutein ester microcapsules; and solidifying the semi-finished lutein ester microcapsules to obtain the lutein ester microcapsules.

Preferably, the extracting solvent is n-hexane, acetone, methyl ethyl ketone, ethyl acetate, or propyl acetate.

Preferably, the washing solvent is ethanol, ethylene glycol, propylene glycol, isopropanol or a mixture thereof.

Preferably, the oil-phase antioxidant is vitamin E.

Preferably, the crude lutein ester has a lutein ester concentration of 45-70%.

Preferably, the wall material, the emulsifier, the water-phase antioxidant, the water-phase filler and water is heated 60° C. to 85° C. to obtain the water phase; the high-speed shearing has a speed of 4000-10000 revolutions per minute, and the homogenizing is conducted under a pressure of 20-60 Mpa; the lutein ester emulsion is dried at 60-120° C. at a feed rate of 10 to 90 mL per minute; and the semi-finished lutein ester microcapsules are solidified at −18° C. to 120° C. for 30 minutes to 24 hours.

Preferably, the vegetable oil is soybean oil, corn germ oil, perilla oil, or a mixture thereof.

Preferably, the wall material is a sugar or a vegetable gum; the emulsifier is sucrose fatty acid ester, modified soybean phospholipid, monopalmitate, sodium stearoyl lactylate, or a mixture thereof the water-phase antioxidant is vitamin C; and the water phase filler is white sugar, glucose syrup, oligomaltose, or a mixture thereof.

Preferably, the sugar is modified starch, maltodextrin, or cyclodextrin, and the vegetable gum is acacia gum, sesbania gum, or guar gum.

Water-soluble lutein ester microcapsules are prepared according to the method of present application.

Preferably, the water-soluble lutein ester microcapsules includes: 1 part of crude lutein ester, 0.03-2.0 parts of the oil phase antioxidant, 1-10 parts of the vegetable oil, 1-50 parts of the wall material, 0.1-8 parts of the emulsifier, 0.02-2.0 parts of the water-phase antioxidant, 0.2-50 parts of the water-phase filler, and 10-200 parts of water.

The advantages of the present invention compared with the prior art are:
1. Because the method of directly extracting lutein esters from marigold granules is adopted, the technical problem of requirements for expensive and complex extraction equipment in the prior art is effectively solved, and the technical effects of low equipment requirements and simple process are realized.
2. Because the method of directly extracting lutein esters from marigold granules is adopted, the technical problem of high cost of preparing lutein ester in the prior art is effectively solved, and the marigold flower particles are easy to store. After extraction, the lutein ester can directly enter the preparation section through the pipeline to obtain microencapsulated particles. The production capacity is not affected. There is no significant difference in product quality between the method of present invention and the method using pure lutein ester, but the cost can be greatly reduced.
3. Because the method of directly extracting lutein esters from marigold granules is adopted, the problem associated with high-purity lutein ester in the prior art that requires high transportation and storage cost is effectively solved. In the present invention, the content of the obtained lutein ester can be controlled. When developing low-content (0.5%-5%) lutein ester microcapsule products, no further purification of the lutein ester is required, and it only needs to be controlled in an appropriate range to facilitate preparation of the products.

DETAILED DESCRIPTION

The examples of this application provide a method for extracting lutein ester and preparing water-soluble lutein ester microcapsules, which solves the problem of high costs in the large-scale mass production of lutein ester microcapsules in the prior art. In the preparation method, lutein ester is first extracted from marigold flower particles, and then a series of steps are used to prepare water-soluble lutein ester microcapsules. In the extraction step, the lutein ester is directly extracted from marigold flower particles. The retention of the medicinal value of marigold flower particles and the increase the health benefits of lutein ester are achieved. At the same time, the use of the twice embedding (drying twice) can also make the prepared capsules more stable and easier to store, suitable for food, medicine and other fields, which greatly reduces the production cost of lutein ester microcapsules.

1. Preparation of Lutein Ester

Example 1

Weighing 100 g of marigold flower particles, adding 1.5 L of ethyl acetate to a 2 L round bottom flask, stirring and refluxing in a 85° C. water bath, mixing ethyl acetate and marigold flower particles to extract lutein ester and other fat-soluble substances until collected ethyl acetate becomes colorless. After the extraction was complete, ethyl acetate was recovered to obtain a crude lutein ester extract. The crude lutein ester extract was washed with a mixture of ethylene glycol:propylene glycol=1:1 for 3 times, and the solvent was then recovered by heating in vacuum. A small amount of antioxidant (vitamin E) was added and mixed to obtain 48% lutein ester.

Example 2

Weighing 100 g of marigold flower particles, adding 1.5 L of n-hexane into a 2 L round bottom flask, stirring and refluxing in a water bath at 80° C., and mixing ethyl acetate with marigold flower particles to extract lutein ester and other fat-soluble substances until collected ethyl acetate becomes colorless. After the extraction was complete, ethyl acetate was recovered to obtain a crude lutein ester extract. The crude extract was washed with a mixture of ethanol:propylene glycol=5:1 for 7 times, and the solvent was recovered by heating in vacuum. A small amount of antioxidant (vitamin E) was added and mixed to obtain 59.5% lutein ester.

Example 3

Weighing 100 g of marigold flower particles, adding 1.5 L of acetone into a 2 L round bottom flask, stirring and refluxing in a water bath at 65° C., and mixing ethyl acetate with marigold flower particles to extract lutein ester and other fat-soluble substances until collected ethyl acetate becomes colorless. After the extraction was complete, ethyl acetate was recovered to obtain a crude lutein ester extract. The crude extract was washed with ethanol for 9 times, and the solvent was recovered by heating in vacuum. A small amount of antioxidant (vitamin E) was added and mixed to obtain 69% lutein ester (E1102).

2. Preparation of Water-Soluble Lutein Ester Microcapsules from the Above Lutein Ester Example 1

Weighing 20 g of 48% lutein ester (E768) and mixing it with 1 g of natural vitamin E into a beaker, adding 40 g of soybean oil to form a mixture, stirring and heating the mixture at 90° C. for 20 minutes to completely dissolve components in the mixture to obtain a lutein ester oil phase. Weighing 100 g of modified starch, 70 g of maltodextrin, 2 g of vitamin C, and 25 g of white granulated sugar into 500 mL of deionized water, stirring and heating at 60° C. for 15 min to obtain a water phase, adding the lutein ester oil phase to the water phase, adding 2 g of emulsifier (sucrose fatty acid ester:sodium stearoyl lactylate=2:1), shearing at 6000 r/min for 10 min to form a colostrum, homogenizing twice under a pressure of 30 MPa to obtain a uniform emulsion, and then embedding and drying the emulsion twice. The drying conditions were: inlet air: 60-70° C., feed rate: 10 mL per minute. The obtained particles were passed through standard sieves of different meshes, and lutein ester microcapsules of different particle sizes were obtained. The lutein ester microcapsules were solidified at −16° C. for 12 hours to obtain water-soluble lutein ester microcapsules.

Example 2

Weighing 50 g of 59.5% lutein ester (E952) and mix it with 2.3 g of natural vitamin E into a beaker, adding 80 g corn germ oil to form a mixture, stirring and heating the mixture at 90° C. for 20 minutes to completely dissolve components in the mixture to obtain a lutein ester oil phase. Weighing 300 g of guar gum, 200 g of cyclodextrin, 3 g of vitamin C, and 55 g of glucose syrup, adding 800 ml of deionized water, stirring and heating at 60° C. for 25 min to obtain a water phase, adding the lutein ester oil phase to the water phase, adding 5.6 g for emulsification (Sucrose fatty acid ester:modified soybean phospholipid=0.5:1), shearing at 7800 r/min for 10 min to form a colostrum, homogenizing 3 times under a pressure of 30 MPa pressure to obtain a uniform emulsion, and then embedding and drying the emulsion twice. The drying conditions were: air inlet: 60-70° C., feeding rate: 15 mL per minute. The obtained particles were passed through standard sieves of different meshes, and lutein ester microcapsules of different particle sizes were obtained. The lutein ester microcapsules were solidified at −8° C. for 18 hours to obtain water-soluble lutein ester microcapsules.

Example 3

Weighing 50 g of 59.5% lutein ester ointment (E952) and mixing it with 4 g of natural vitamin E into a beaker, adding 120 g of (perilla oil:peanut oil=1:2) to form a mixture, stirring and heating at 100° C. for 10 minutes to completely dissolve components in the mixture to obtain a lutein ester oil phase. Weighing 400 g of gum arabic, 110 g of sesame gum, 3 g of vitamin C, and 35 g of white granulated sugar into 800 mL of distilled water, stirring and heating at 70° C. for 15 min to obtain a water phase, adding the lutein ester oil phase to the water phase, adding 5.5 g emulsifier (monopalmitate:sodium stearoyl lactylate=1:1), shearing at 7800 r/min for 10 min to form a colostrum, homogenizing twice under a pressure of 55 MPa to obtain a uniform emulsion, and embedding and drying the emulsion twice. The drying conditions were: inlet air: 80-90° C., feeding rate: 10 mL per minute. The obtained particles were passed through standard sieves of different meshes to obtain lutein ester microcapsules of different particle sizes. The lutein ester microcapsules were solidified at 56° C. for 9 hours to obtain water-soluble lutein ester microcapsules.

Example 4

Weighing 100 g of 69% lutein ester (E1102) and mix it with 4 g of natural vitamin E into a beaker, adding 180 g of (corn germ oil:perilla oil=3:1) to form a mixture, stirring and heating at 110° C. for 8 minutes to completely dissolve components in the mixture to obtain a lutein ester oil phase. Weighing 500 g of modified starch, 200 g of gum arabic, 3 g of vitamin C, and 65 g of maltooligosaccharides into 1100 mL of distilled water, stirring and heating at 80° C. for 30 min to obtain a water phase, adding the lutein ester oil phase to the water phase, adding 7.5 g of emulsifier (sucrose fatty acid ester:sodium stearoyl lactylate:monopalmitate=1:1:1), shearing at 10000 r/min for 1 3 min to form a colostrum, homogenizing 4 times under a pressure of 45 MPa to obtain a homogeneous emulsion, and embedding and drying the emulsion twice. The drying conditions were: inlet air: 95-105° C., feeding rate: 35 mL per minute. The obtained particles were passed through standard sieves of different meshes, and lutein ester microcapsules of different particle sizes were obtained. The lutein ester microcapsules were solidified at 115° C. for 2 hours to obtain water-soluble lutein ester microcapsules.

In the stability application test, the water-soluble lutein ester microcapsules of the present application and conventional spray-dried powder were stored for 24 hours, 48 hours, 72 hours. Under the conditions of non-vacuum packaging and sealing and dark storage at an ambient temperature of 55° C., the content loss ratio of water-soluble lutein ester microcapsules was 0%, 0.03%, 0.18%, and the content loss ratio of conventional spray-dried powder was 0.53%, 2.97%, and 7.29%. The conventional spray-dried powder had slight oil and grease leakage. It can be seen that the product stability of water-soluble lutein ester microcapsules is greatly improved compared with conventional spray-dried powder, and the requirements for transportation and storage conditions are low, and the shelf life of the product is increased in practical applications.

Finally, it should be noted that: obviously, the above-mentioned embodiments are merely examples for clearly illustrating the present invention, rather than limiting the implementation manners. For those of ordinary skill in the art, other changes or changes in different forms can be made on the basis of the above description. There is no need and cannot give an exhaustive list of all implementation methods. The obvious changes or modifications derived from this are still within the protection scope of the present invention.

The invention claimed is:

1. A method of preparing water-soluble lutein ester microcapsules, comprising:
   mixing marigold flower particles with acetone, refluxing at 65° C.;
   mixing ethyl acetate with the marigold flower particles to extract until collected ethyl acetate becomes colorless;
   removing ethyl acetate to obtain a crude extract;
   washing the crude extract with ethanol;
   removing ethanol to obtain a crude lutein ester;
   adding vitamin E and a mixture of corn germ oil and *perilla* oil with a weight ratio of 3:1 to the crude lutein ester, mixing and heating at 110° C. to obtain a lutein ester oil phase;
   adding a wall material, an emulsifier, a water-phase antioxidant, and a water-phase filler into water, and heating to obtain a water phase;
   adding the lutein ester oil phase to the water phase under a high-speed shearing, mixing evenly, and homogenizing by a high-pressure homogenizer to obtain a lutein ester emulsion;
   drying the lutein ester emulsion twice to obtain semi-finished lutein ester microcapsules; and
   solidifying the semi-finished lutein ester microcapsules to obtain the lutein ester microcapsules,
   wherein the wall material, the emulsifier, the water-phase antioxidant, the water-phase filler and water is heated at 80° C. for 30 minutes to obtain the water phase; the high-speed shearing has a speed of 10000 revolutions per minute for 13 minutes, and the homogenizing is conducted 4 times under a pressure of 45 MPa; the lutein ester emulsion is dried at 95-105° C. at a feed rate of 35 mL per minute; and the semi-finished lutein ester microcapsules are solidified at 115° C. for 2 hours;

wherein the crude lutein ester has a lutein ester concentration of 69%; and wherein the wall material is modified starch, the emulsifier is gum arabic, the water-phase antioxidant is vitamin C, and the water-phase filler is maltooligosaccharides.

* * * * *